United States Patent [19]

Sirany

[11] Patent Number: 4,987,127
[45] Date of Patent: Jan. 22, 1991

[54] METHOD OF TREATING A VIRUS OUTBREAK

[76] Inventor: Dal Sirany, 5733 Dumas Ave., Minnetonka, Minn. 55345

[21] Appl. No.: 304,768

[22] Filed: Jan. 31, 1989

[51] Int. Cl.$^5$ ............................................. A01M 37/36
[52] U.S. Cl. .................................................... 514/159
[58] Field of Search ........................................ 514/159

[56] References Cited

U.S. PATENT DOCUMENTS

| | | | |
|---|---|---|---|
| 1,915,945 | 6/1933 | Nitardy | 514/164 |
| 2,056,208 | 10/1936 | Putt | 167/65 |
| 3,119,739 | 1/1964 | Campbell | 167/58 |

OTHER PUBLICATIONS

The American Medical Association Family medical Guide, 1987 Ed. p. 459.
Essential Guide to Prescription Drugs, 1987, pp. 126-129.

Primary Examiner—Stanley J. Friedman
Assistant Examiner—T. J. Criares
Attorney, Agent, or Firm—Kinney & Lange

[57] ABSTRACT

A pharmaceutical product and a method for treating an outbreak of virus is disclosed. The pharmaceutical product comprises acetylsalicylic acid and water. The pharmaceutical product is applied to the epidermis or mucous membrane region involved in the outbreak of the virus. A kit facilitating prompt and convenient preparation of the inventive pharmaceutical product and facilitating treatment is also disclosed.

15 Claims, No Drawings

METHOD OF TREATING A VIRUS OUTBREAK

FIELD OF THE INVENTION

The present invention relates to the treatment of virus outbreak or flare-up episodes and in particular to a method and pharmaceutical product for the treatment of flare-up or outbreak episodes of herpes simplex and related viruses.

BACKGROUND OF THE INVENTION

Herpes viruses are a group of DNA-containing animal viruses that produce disease, the best known of which is herpes. The viral disease, herpes, is characterized by eruptions of the skin or mucous membrane. Such eruptions are painful, unsightly, and associated with spread of the virus. Examples of various types of herpes viruses are herpes simplex or herpes zoster (responsible for the disease shingles).

The virus typically has two major phases, a dormant phase in which the disease state is not observable, and an active phase in which the virus "flare-up" or "breaks out" of the dormant phase to cause the characteristic herpes eruptions on the skin or mucous membranes of an individual.

During the active phase, an outbreak progresses through a number of sub-steps. First, the epidermis or mucous membrane in the area becoming involved in the outbreak becomes itchy or burns. Other symptoms, often associated with the early sub-steps of an outbreak, include tingling or numbness of the affected area. Second, the area becoming involved turns red and/or appears inflamed. Additionally, late in the second sub-step, subsurface lumps begin to form in the affected area. Next, in the third sub-step, blisters or vesicles begin to erupt or appear on the surface of the skin. Late in the third sub-step, the blisters or vesicles rupture, releasing a clear liquid and leaving an open sore at the site of the ruptured blister. This period of time, late in the third sub-step is sometimes referred to a "full bloom." Subsequently, in the forth sub-step, the outbreak progresses to a scab formation step. Later, in a fifth sub-step, the scab drops off, leaving tender new skin or mucous membrane. After the scab has fallen off, in the fifth step, the skin or mucous membrane of the involved area reverts to normal tissue.

A significant portion of the population is infected with Herpes virus and outbreaks in infected individuals occur intermittently throughout the remainder of their lives.

Acetylsalicylic acid is a well known drug, available as an over-the-counter pharmaceutical product in the United States. Acetylsalicylic acid is most commonly employed in an ingestible form for analgesic purposes. Acetylsalicylic acid has also been used as a surface supplied analgesic. The Nitardy patent, U.S. Pat. No. 1,915,945, suggests the use of acetylsalicylic acid in an ethyl ether and oil base for application to mucous membranes. The patent further suggests a synergistic action between acetylsalicylic acid and ethyl ether.

The Putt patent, U.S. Pat. No. 2,056,208, discloses that acetylsalicylic acid is known for application to mucous membranes of the mouth. The Putt patent also discloses the application of a liniment, including acetylsalicylic acid, to unbroken skin as a liniment for the treatment of inflammation or pain and to provide an analgesic effect. This patent further teaches that acetylsalicylic acid rapidly breaks down in water to salicylic acid and acetic acid. The rapid breakdown of acetylsalicylic acid is considered undesirable by Putt who suggests the need to use acetylsalicylic acid in a liquid form which does not allow a degradation or breakdown during the time required for absorption through the skin. The particular liniment disclosed is 30 grains in 1 ounce of glycerol oleate or other "unctuous base". The patent further discloses testing for absorption of acetylsalicylic acid by a ferric chloride reaction with any acetylsalicylic present in the urine and by fluorescence of skin which has absorbed acetylsalicylic acid.

The Campbell patent, U.S. Pat. No. 3,119,739 discloses the use of a composition, including acetylmethyl-salicylate, for pain relief and as an anodyne agent. The patent includes the statement that "it should be understood in no sense be regarded as a curative agent for the basic cause of the pain." The acetylmethyl-salicylate is used as 1–20% mixture in an inert pharmaceutical carrier. Solvents for the acetylmethyl-salicylate are preferred as the pharmaceutical carrier but suspensions or emulsions may also be used. Examples of suitable inert pharmaceutical carriers are ethanol, isopropanol and polyethylene glycol. The mixture is useful for treating insect bites and allergic reactions.

A popular over-the-counter lip ointment sold under the trademark BLISTEX by Blistex Incorporated of Oakbrook, Ill. 60521 contains allantoin (1%), camphor (0.5%) and phenol (0.5%) in an emollient base with petrolatum, lanolin, menthol, methyl salicylate, and other ingredients.

In spite of such prior art disclosing the use of acetylsalicylic acid and related compounds such as methyl salicylate and acetyl methyl salicylic acid as analgesic and anti-inflammatory agents for both internal and external application, the prior art has not taught nor suggested use of externally applied acetylsalicylic acid as a treatment for herpes-type virus diseases. Further, the prior art has taught away from pharmaceutical preparations including both acetylsalicylic acid and water because of the fear of rapid degradation of the acetylsalicylic acid component into acetic acid and salicylic acid.

SUMMARY OF THE INVENTION

The present invention includes a method for treating a virus outbreak. By "treatment", is meant that not only the pain associated with the outbreak is reduced, but also that either the duration or the severity of the outbreak is reduced. In some situations, the progression of the outbreak through the typical course of sub-steps is altered. However, the term "treatment" is not intended to convey an alleviation of infection by the virus in currently infected individuals. In other words, an individual infected with a herpes virus will continue to be infected with the virus and may still suffer from outbreaks of the active virus, although the outbreaks can be modified by the treatment method of this invention. By "outbreak" is meant the active phase of the virus and the characteristic disease associated with the virus in the active state, as specifically contrasted with the virus in the dormant phase.

The present invention also includes a method for preventing a virus outbreak at a body surface. The method includes applying acetylsalicylic acid to the body surface. By "preventing a virus outbreak" is meant that many of the typical symptoms of later sub-steps of an outbreak may be avoided. The prevention method again involves application of acetylsalicylic acid to the area of the body which is to be protected from the outbreak. For example, prompt application of acetylsalicylic acid during the initial recognition of the first sub-step of an outbreak prevents some or all of the subsequent sub-steps.

A preferred embodiment of the method of treatment or prevention of the present invention includes the step of applying a paste formed of acetyl-salicylic acid and water to the epidermis or mucous membrane proximal or immediately adjacent the body area involved or about to be involved in an outbreak.

The present invention also includes a pharmaceutical preparation or paste for the treatment of a virus outbreak comprising acetyl-salicylic acid and water. The present invention also includes a kit for the treatment of a virus outbreak comprising a quantity of acetylsalicylic acid and a container sufficient to form the pharmaceutical paste of the present invention. Preferably, the kit further includes instructions and most preferably further includes a quantity of water for mixing with the acetylsalicylic acid of the kit.

DETAILED DESCRIPTION

The method of the present invention provides a number of beneficial effects in the treatment of a virus outbreak. First, the method reduces the duration of the virus outbreak, either by shortening the duration of the sub-steps or by altering the course of the outbreak. Second, the method reduces the severity of the virus outbreak. Third, the method reduces the pain associated with an outbreak.

A pharmaceutical preparation of the present invention is a paste prepared from acetylsalicylic and water. Preferably, the paste should be freshly prepared before application. By freshly prepared is meant that paste should be used within about 1 hour of preparation and preferably within 30 minutes and most preferably the first application of paste to the affected region should be made within about 1-5 minutes of preparation of the paste, with the remaining paste used for reapplication during a single treatment period of preferably about 30 minutes. The acetyl-salicylic acid used to form the paste may be present as purified powdered acetyl-salicylic acid or alternatively as a tablet. Such tablets typically include starch or other tableting agents for holding the acetyl-salicylic acid in a tablet form. Although coated or buffered aspirin products may be used to form the powder component of the paste of this invention, they are believed to be somewhat less efficient than traditional aspirin tablets. In all cases, the acetyl-salicylic acid should be reduced or ground to a fine powder.

The other major component of the paste is water. Preferably the water is present as distilled water although any potable water such as tap water may be suitably employed to prepare the paste of the present invention. Tap water is believed to be somewhat less efficient than distilled water. Additionally, a low microbial content in the water used in paste formation is believed to be desirable for avoiding possible secondary infections in the individual to be treated. The paste is prepared by mixing the powdered acetylsalicylic acid and the water together and stirring vigorously to obtain a stiff, thick and somewhat adherent slurry. Proportions of acetylsalicylic acid to water may be from about 1.63:1.00 to about 0.26:1.00, with proportions of about 0.81:1.00 being preferred. The amount of paste prepared should be adequate to more than cover the affected area.

In one embodiment, a single tablet of about 325 milligrams (about 5 grains) of acetylsalicylic acid was crushed and then reduced by grinding to a fine powder. Approximately 0.40 ml of distilled water was added to the powder and the resulting powder and liquid mixture stirred until fully blended, for about 1 minute, to obtain a stiff paste. The paste prepared was more than adequate for a single treatment application to a typical outbreak.

The paste of the present invention is applied to the affected area of an outbreak during any of the sub-steps of the active phase of the virus. Preferably, the application is performed during the early sub-steps of a virus outbreak. Early stages of a virus outbreak are typically detected by a patient as a localized burning and/or itching sensation. The paste is applied to the area of the skin about to be affected or being affected by the virus outbreak as a layer, preferably about 1.6 mm in thickness upon the skin or epidermis.

However, effective application layers can range from about 0.02 mm in thickness up to as much as perhaps 10 mm in thickness. Thinner layers may require additional applications of the paste to provide optimal treatment, whereas extremely thick layers may be difficult to maintain in their adhering relationship with the affected area.

Subsequent to application of the paste to the area of the viral outbreak, the paste generally begins to dry out. The dried paste tends to lose its adherence to the skin or epidermis and falls off of the affected area. Preferably, any paste which is dried and fallen off should be recovered with additional paste.

The application of the paste is maintained for a suitable period time, preferably about twenty to thirty minutes of treatment time. Typically, during the treatment period, the paste will dry out and require a renewed application of the paste. After the treatment period has expired, the paste typically will be effectively dried out and may be lightly brushed or abraded off of the skin. Excessive brushing should be avoided as it may tend to irritate the affected skin or epidermis.

After brushing off most of the dried paste, the treated skin area should be gently cleansed with water. The water cleansing action tends to remove any remaining residue of the paste.

The treatment should be repeated as symptoms of the outbreak occur. Preferably, the application of the paste of this invention should be repeated several times per day. Typically, for example, effective treatment is obtained employing from about two to about six applications per day, as symptoms occur, until the symptoms of the virus outbreak are no longer present. Preferably, four treatments per day of approximately 30 minutes each treatment and continuing at that frequency of treatment for the course of the outbreak is believed by the inventor to be most effective in treating an outbreak.

EXAMPLES

Example 1

Test subject A., a male caucasian, approximately fifty five years of age, with a history of intermittent "cold sores", was treated in various stages of different outbreaks.

(1.a.) In one episode with the subject, A., a paste of this invention was applied for thirty minutes during the pre-blistering sub-step or burning stage of a cold sore. A second application was made one-half day later for twenty minutes. Blistering or scabbing did not appear subsequently in the treated area. This episode is an example which may be termed a prevention of a virus outbreak.

(1.b.) In another episode, the same subject, A. was treated at the first observance of visible blisters. The treatment was repeated once several hours later and resulted in a small (i.e., about 2 mm) scab forming.

(1.c.) In yet another episode with the same subject, A., a single small blister was observed and immediately treated with a twenty minute application of the paste. A few hours later, no evidence of the blister was detectable. No cold sore nor scab developed subsequent to this treatment. This is an episode which may be termed a prevention of a virus outbreak.

(1.d.) In another episode with the same subject, A., application of the paste of this invention was applied for thirty minutes to a cold sore in the earlier visible blistering stage. A few minutes after the paste was brushed away and washed off of the blistered area, the blistering symptoms were relieved. Several hours later the paste of the present invention was reapplied to the same area and the treatment repeated. The following morning a scab formed; the scab came off four to five days later with no complications.

(1.e.) In yet another episode with the same subject, A., the outbreak was allowed to proceed to well into late sub-step 3 (which may alternatively be described as a "full bloom" of blisters) prior to initiating treatment by the method of this invention. At that point, a paste formed of a 5 grain tablet of acetylsalicylic acid and distilled water was applied for thirty minutes. Related sensations (i.e. burning, itch and pain) disappeared and scab formation occurred about two days later and the scab came off approximately five days later with no apparent complications.

(1.f.) In yet another episode with same subject, A., an outbreak (cold sore) was allowed to proceed for approximately eight hours after the first symptoms were observed, i.e. the outbreak was in sub-step 2. The paste was applied. Within twenty-four hours a small (i.e. 2 mm diameter approximately) scab was formed. A second application of the paste was administered. The scab came off approximately four days later.

(1.g.) During the stage of a cold sore outbreak episode in which a cold sore was beginning to scab, (i.e. sub-step 4) a paste was prepared by combining a 5 grain Bayer brand acetylsalicylic acid tablet and about 0.40 ml of tap water. The paste was applied to the scab and the application maintained for approximately twenty minutes. At the end of twenty minutes, the dried paste was brushed off, the area washed lightly with water. Within a few hours, the scabbing process appeared to be greatly accelerated (i.e. the duration of sub-steps after application of the paste decreases relative to a typical untreated outbreak.)

Example 2

Subject, B., a male caucasian, approximately eight years of age, genetically related to subject A., with a history of intermittent episodes of cold sore/herpes simplex outbreaks was treated during various sub-steps of herpes outbreaks.

(2.a.) In one episode, subject B. was treated with two thirty minute treatments per day beginning just prior to the development of the blister stage of the cold sores, (i.e. sub-step 2.) The symptoms were completely controlled and gone by the fifth day.

(2.b.) In another episode with subject B., a white blister, about 3 mm in diameter (sub-step 3) was treated with a single application in the morning and two evening applications of the paste of this invention. The next day, the symptoms of a typical cold sore did not appear.

(2.c.) In another episode with subject B., an outbreak consisting of two single blisters, one on the lip and one on the nostril, were observed. The blisters (sub-step 3) were treated with the paste of this invention for thirty minutes. The blister on the lip was reduced in size and all itching was gone later the same day. The blister on the nostril was reduced in size and the itching and other associated symptoms were also gone later in the day. The next day only slight redness existed in the areas where the blisters had previously been present. One day later all evidence of an outbreak was gone. Example 3

The subject, C., a caucasian female of approximately forty three years of age, genetically related to subject B., but not to subject A., with a history of intermittent outbreaks of herpes simplex was treated by the method of the present invention during various stages of virus outbreaks.

(3.a.) In an outbreak episode, subject C. experienced the burning sensation indicating an early stage of a viral outbreak (sub-step 1). Thirty minute applications of the paste were applied and no symptoms subsequently developed in that episode. This episode may be termed an example of prevention of a virus outbreak.

(3.b.) In a subsequent episode, a single blister appeared on subject C (i.e. sub-step 3). The paste of this invention was promptly applied. A second set of blisters appearing at a different part of the lip were also treated by the method of this invention. The next day the eruptions appeared greatly reduced and mostly reddened. Subsequent fifteen minute applications of the paste of the present invention were made on the second day. By the afternoon of the second day, a thirty minute application was made to observable blisters. However, the blisters were reduced in area and other symptoms were not present. By the third day blisters were gone and slight scab and tenderness was observable on one lip. C.'s other lip began to demonstrate a burning sensation indicative of an early stage of an outbreak. The area was not subsequently treated and turned into a typical cold sore episode.

(3.c.) During one of subject C.'s outbreak episodes, an application of the paste was made. The outbreak had already progressed to the development of scabs (i.e. sub-step 4). An additional application was made that evening and left on all night. The next day the scab fell off completely leaving clean pink surface. Treatments were continued and a new scab formed approximately ¼ inch in diameter. The patient indicated the scab was not uncomfortable and the scab did not increase in size. The treatments were continued and on approximately the seventh day all symptoms of the outbreak were gone.

(3.d.) In a subsequent outbreak episode of subject C., the paste of this invention was applied for twenty minutes at the first observance of the pain, itching, and burning sensation indicative of an early sub-step of the cold sore development (sub-step 1 or 2). A slight swelling appeared to be present prior to the application. Treatments were discontinued and two days later blisters and scabs formed in the area. On the fourth day, application of the paste was recommenced. The cold sore was completely cleared three days later.

CONCLUSION

The method of this invention is an effective treatment for outbreaks of herpes virus. When the treatment is initiated and maintained at the onset of an outbreak episode, the method may alter the course of the outbreak episode by avoiding some of the sub-steps which would typically follow the early sub-steps. Where the symptoms typically associated with later sub-steps of an outbreak, for example, blisters, ruptured blisters, or scabbing are avoided, the method of the present invention may be termed a method for preventing a virus outbreak. Specifically, if the outbreak has not progressed to the extent that any sub-surface lumps have formed and no blisters have yet formed, rupturing blisters and scab formation will generally be avoided by treatment with the disclosed method. In instances where sub-surface lumps have formed but blisters have not yet formed, treatment by the method of the present invention will result in avoidance of ruptured blisters and only small scabs (i.e. approximately 1-2 mm in diameter) will form. The small scab will generally fall off after about 4 to 5 days. In cases where the outbreak has proceeded to blister formation, treatment by the method of this invention prevents significant rupturing of the blisters. In instances in which the cold sore had progressed to a "full bloom" stage, i.e. rupturing blisters, the treatment method of this invention reduced the duration of the rupturing of blisters and the outbreak proceeds to an accelerated scabbing sub-step. Thus shorting the overall time frame of the outbreak. Additionally, the method of the present invention offers the individual suffering from an outbreak significant relief from the pain associated with a outbreak.

It is also believed that treatment by the method of this invention would be effective in treating other herpes-type outbreaks, for example, genital herpes and herpes zoster (commonly known as shingles). Diseases which may be effectively treated by the drug acyclovir, (sold under the brand name ZOVIRAX), would potentially be effectively treated by the method of the present invention.

The components required to prepare the pharmaceutical paste of this invention may be conveniently supplied as a kit which will provide an infected individual with the ability to begin treatment of an outbreak of the virus promptly upon recognition of the early symptoms of an outbreak. Specifically, such a kit would contain a portion of powdered acetyl salicylic acid. Preferably, a portion of distilled water or other suitable water would also be included in the kit. At least one of the portions of the components would be contained in a container suitable for mixing the two components into a paste. Preferably, the kit of this invention would further include instructions for the preparation of the pharmaceutical paste and instructions for effective application of the paste to the area of an outbreak.

Although the present invention has been described with reference to preferred embodiments, workers skilled in the art will recognize that changes may be made in form and detail without departing from the spirit and scope of the invention.

What is claimed is:

1. A method of treating a herpes virus outbreak at an affected area of a body surface, the method comprising:
   applying an effective amount of a paste containing acetylsalicylic acid and water in a layer having a thickness of between about 0.2 mm and 10 mm over the affected area; and
   maintaining the paste in contact with the affected area for a treatment period sufficient to affect development of the herpes virus outbreak.

2. The method of claim 1 wherein the treatment period is between about 20 minutes and about 30 minutes.

3. The method of claim 2 and further comprising:
   removing the paste from the affected area after the treatment period is complete.

4. The method of claim 3 wherein the removing comprises:
   permitting the paste to dry; and brushing the dried paste off the affected area.

5. The method of claim 4 wherein removing further comprises:
   cleaning the affected area with water to remove any residue of the paste.

6. The method of claim 2 and further comprising:
   periodically repeating the applying and maintaining steps a number of times until the outbreak has subsided.

7. The method of claim 1 wherein the paste contains acetylsalicylic acid and water in proportions of about 1.63:1.00 to about 0.26:1.00.

8. A method of treating a herpes virus outbreak at an affected area of a body surface, the method comprising:
   covering the affected area with a layer having a thickness of between about 0.02 mm and about 10 mm of an effective amount of a paste containing as an active ingredient acetylsalicylic acid in a concentration sufficient to affect development of the herpes virus outbreak; and
   maintaining the paste in contact with the affected area for a treatment period sufficient to affect development of the herpes virus outbreak.

9. The method of claim 8 wherein the paste consists essentially of acetylsalicylic acid and water.

10. The method of claim 9 wherein proportion of the acetylsalicylic acid and the water are about 1.63:1.00 to about 0.26:1.00.

11. The method of claim 8 wherein the treatment period is at least about 20 minutes.

12. The method of claim 8 and further comprising:
    permitting the paste to dry; and
    brushing the dried paste off the affected area.

13. The method of claim 12 and further comprising:
    cleansing the affected area with water to remove any residue of the paste.

14. The method of claim 8 and further comprising:
    periodically repeating the covering and maintaining steps.

15. A paste for direct application in a layer having a thickness of between about 0.02 mm and about 10 mm to an affected area of a body surface for a period of about 20 minutes to about 30 minutes to treat an outbreak of a herpes virus at the affected area, the paste consisting essentially of acetylsalicylic acid and water in proportions of about 1.63:1.00 to about 0.26:1.00.

* * * * *